(12) United States Patent
Isgro

(10) Patent No.: US 9,060,598 B2
(45) Date of Patent: *Jun. 23, 2015

(54) LABORATORY TABLE HAVING TABLETOP ELEMENTS

(71) Applicant: Tecan Trading AG, Mannedorf (CH)

(72) Inventor: Claudio Isgro, Duernten (CH)

(73) Assignee: Tecan Trading AG, Mannedorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/055,550

(22) Filed: Oct. 16, 2013

(65) Prior Publication Data

US 2014/0083337 A1  Mar. 27, 2014

Related U.S. Application Data

(63) Continuation-in-part of application No. 13/550,900, filed on Jul. 17, 2012, now Pat. No. 8,584,602.

(30) Foreign Application Priority Data

Jul. 21, 2011  (CH) ....................................... 1219/11

(51) Int. Cl.
*A47B 13/00* (2006.01)
*A47B 13/08* (2006.01)
*B01L 9/02* (2006.01)
*G01N 35/00* (2006.01)

(52) U.S. Cl.
CPC ................. *A47B 13/088* (2013.01); *B01L 9/02* (2013.01); *B01L 2200/025* (2013.01); *B01L 2200/028* (2013.01); *B01L 2300/0829* (2013.01); *G01N 2035/00306* (2013.01)

(58) Field of Classification Search
CPC ........... A47B 3/12; A47B 3/06; A47B 87/002
USPC ............. 108/157.18, 157.17, 157.15, 159.11, 108/157.1, 157.16, 158.13, 158.12; 248/188
See application file for complete search history.

(56) References Cited

U.S. PATENT DOCUMENTS

| 795,957 A | 8/1905 | Cartland |
| 1,793,709 A | 2/1931 | Meyers |

(Continued)

FOREIGN PATENT DOCUMENTS

| JP | 8131852 | 5/1996 |
| JP | 11137344 | 5/1999 |

(Continued)

*Primary Examiner* — Jose V Chen
(74) *Attorney, Agent, or Firm* — Notaro, Michalos & Zaccaria P.C.

(57) ABSTRACT

Laboratory table has a frame with front and rear frame parts, at least one detent element, at least one detent extension and at least one replaceable tabletop element on the frame. Each tabletop element has at least one fixing mechanism for interacting with the frame parts and for holding a corresponding detent element and detent extension in fixing positions. A detent element or detent extension in each case is spaced apart from the fixing mechanism. The frame part opposite to the frame part the fixing mechanism is interacting with comprises a detent element or a detent extension that in each case is brought into a mutual fixing position with a corresponding detent extension or detent element of the corresponding tabletop element. The corresponding detent extension is thus guided in a detent element parallel to a tabletop axis of the corresponding tabletop element.

20 Claims, 5 Drawing Sheets

(56) References Cited

U.S. PATENT DOCUMENTS

| | | |
|---|---|---|
| 1,795,138 A | 3/1931 | Ohnstrand et al. |
| 2,973,233 A | 2/1961 | McPhee |
| 3,267,889 A | 8/1966 | Bedol |
| 4,317,416 A | 3/1982 | Baum et al. |
| 4,944,235 A | 7/1990 | Jahnke et al. |
| 5,232,303 A | 8/1993 | Rubner |
| 5,549,055 A | 8/1996 | Kusch |
| 6,082,838 A | 7/2000 | Bissu-Palombo |
| 6,250,842 B1 | 6/2001 | Kruger |
| 6,318,276 B1 | 11/2001 | Reinecke |
| 7,128,493 B2 | 10/2006 | Alarcon-Lopez |
| 8,584,602 B2 * | 11/2013 | Isgro ................ 108/157.18 |
| 2010/0282133 A1 | 11/2010 | Wong |

FOREIGN PATENT DOCUMENTS

| | | |
|---|---|---|
| JP | 2008131852 | 6/2008 |
| JP | 2010178796 | 8/2010 |
| JP | 2011137344 | 7/2011 |

\* cited by examiner

US 9,060,598 B2

LABORATORY TABLE HAVING TABLETOP ELEMENTS

RELATED PATENT APPLICATIONS

This is a Continuation In Part application to the U.S. patent application Ser. No. 13/550,900 that has been filed on Jul. 17, 2012, that has been published as US 2013/0019782 A1, and that claims priority of the Swiss Patent Application No. 01219/11 filed on Jul. 21, 2011, the entire disclosure of these applications is herein incorporated by explicit reference for any purpose.

TECHNICAL FIELD OF THE INVENTION

The invention relates to a laboratory table, in particular for automated laboratory systems, which comprises at least one frame having a front frame part and a rear frame part opposite thereto, as well as a number of tabletop elements positionable on this at least one frame.

Large laboratory facilities, in particular automated laboratory systems, typically comprise a base frame, on which a laboratory tabletop is laid. This laboratory tabletop is used as a work surface for the robot arms, which access the laboratory tabletop from above. The robot arms are typically provided with pipette tips for the transport of liquids or with grippers for the transport of labware, e.g., microplates or sample tubes. The Freedom EVO® Liquid Handling Workstation of the current applicant is mentioned as an example of such a laboratory system. The space below the work surface is often also to be able to be used for additional apparatus, such as centrifuges, incubators, microplate readers, etc. For this purpose, for example, openings are sawn into the tabletop, so that robot arms can access the apparatus below the work surface for the transport of labware (e.g., for loading and unloading of a centrifuge).

RELATED PRIOR ART

Apparatus such as microplate incubators, polymerase chain reaction (PCR) thermocyclers for the amplification of nucleic acids, and solid phase extraction (SPE) modules having comparatively large overall height are frequently located on the work surfaces of such "liquid handling workstations" or "robotic sample processors" (RSP). Some of these apparatuses are so tall that the pipette tips installed on the robot arms can no longer be moved over them. The apparatuses must therefore be detoured as obstructions. If tall apparatuses can be placed on a second, lower work surface, the direct travel routes of the robot arms having pipette tips or grippers remain free.

Very precise alignment of the pipette tips on the robot arm to the wells of the microplates on the work surface is necessary for pipetting in microplates having 384 wells (center-to-center distance 4.5 mm) or 1526 wells (center-to-center distance 2.25 mm). Continuous laboratory tabletops are often provided with detent cams or other holders for positioning so-called "carriers", which carry the labware, e.g., microplates, in order to achieve the required positioning precision.

Laboratory tables having tabletop elements are known from the prior art. According to JP 11-137 344 A1, for example, this relates to the use of office desks as laboratory tables, four office desks being arranged and held by means of a frame in a rectangle and a laboratory tabletop being laid on this frame.

A laboratory table is known from JP 8-131 852 A1, in which no wiring is visible or can obstruct the use of the laboratory table. The worktop of this laboratory table consists of a front part and a rear part, which each rest on a frame corresponding to the size of these partial worktops. The cables for the required electrical connections can be laid in special cable channels.

OBJECTS AND SUMMARY OF THE PRESENT INVENTION

The object of the present invention is to propose an alternative laboratory table, which comprises at least one frame having a front frame part and a rear frame part opposite thereto, as well as tabletop elements positionable on this at least one frame.

This object is achieved according to a first aspect in that a laboratory table having the features as herein disclosed is proposed.

This object is achieved according to a second aspect in that a method having the features as herein disclosed for providing a laboratory table is proposed, this laboratory table comprising at least one frame having a front frame part and a rear frame part opposite thereto, as well as tabletop elements positionable on this at least one frame.

Further features according to the invention and a use according to the invention of a clamping lever result from the dependent claims.

Advantages of the laboratory table according to the invention comprise:

Simple laboratory devices can be equipped with individual or a few tabletop elements.

Larger laboratory devices up to complex laboratory facilities, e.g., so-called "liquid handling workstations" or "robotic sample processors" (RSP) can be equipped with a number of modular tabletop elements.

The modular tabletop elements according to the invention are arbitrarily replaceable and exchangeable in or on a frame which is equipped with the detent rails according to the invention.

The replaceable tabletop elements can very especially comprise equipment and/or structures, so that areas of the work surface of laboratory devices or laboratory facilities can be assigned permanently or also only temporarily to specific workflows.

If a level formed by the installed tabletop elements is defined as the main work level in a large laboratory device or in a complex laboratory facility, additional secondary work levels can be defined above and/or below this main work level and can be equipped with further tabletop elements.

By lowering the tabletop elements to a lower secondary work level, components having a taller installation height can be installed in laboratory facilities, so that the movement range of robots present in these laboratory facilities is impaired substantially less.

Selected areas of the work surface of laboratory devices or laboratory facilities can be left open or equipped with tabletop elements, which have corresponding reach-through openings, to allow the transfer of containers (e.g., for loading/unloading a centrifuge).

Areas having lower work surface adjacent to or between work surfaces of the upper level can be modularly assembled from various existing tabletop elements.

Individual tabletop elements which can be inlaid naturally result in greater tolerances than continuous laboratory tabletops. Mechanical tolerances can add up in an unfavorable manner in this case. Therefore, the tabletop elements are preferably fixed by clamping or bracing in the frame.

By clamping a frame part using a stop surface in a detent rail/detent bolt combination and using the clamping bow of a clamping lever, a friction-locked, blocked fixing of the detent bolt results, without the frame of the laboratory device or the laboratory facility being tensioned or even deformed. The special equipment and/or structures of the tabletop elements and therefore also containers placed on this equipment and/or these structures are preferably positioned exactly.

For every configuration of the automated laboratory system in which the apparatuses are located below the work surface at another location, another laboratory tabletop having altered opening is necessary. The number of the laboratory tabletop variants rapidly becomes larger and larger. Through skilled combination of individual tabletop elements and laboratory table elements, which are of different widths under certain circumstances, having openings, all variants of work surfaces can be modularly assembled.

The modularity of the tabletop elements in combination with the modular grid of the fastening of the detent cams on the tabletop elements and the division of the detent openings in the detent rails allows an arbitrary selection and replaceability of the tabletop elements, so that existing laboratory facilities can also be adapted easily for other intended uses.

BRIEF INTRODUCTION OF THE ATTACHED DRAWINGS

The laboratory table according to the invention will be explained in greater detail on the basis of the appended drawings, these drawings showing exemplary embodiments and not restricting the scope of the present invention. In the attached figures.

Figure 5A:
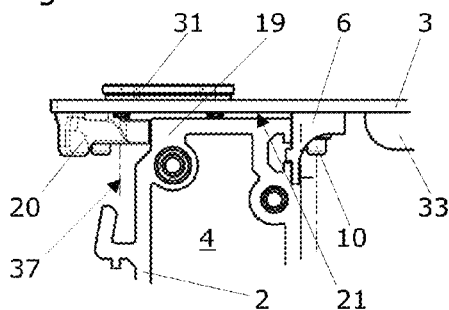
FIG. 5 shows detail sections of FIG. 4.
Figure 5B:
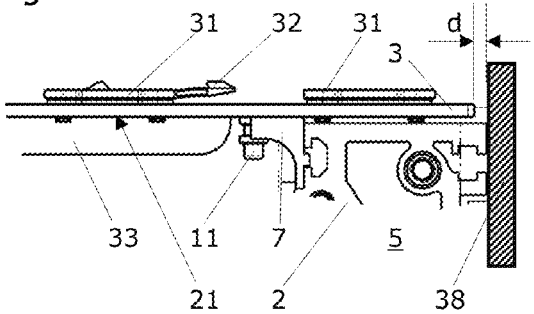
Figure 6A:
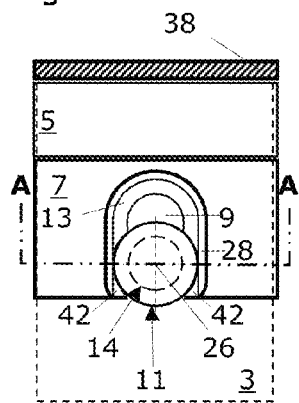
Figure 6B:
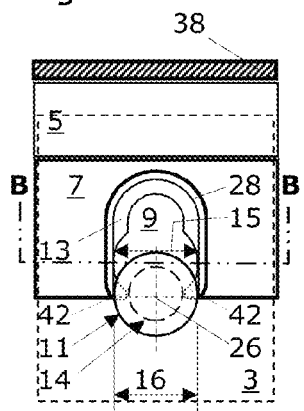
Figure 6C:
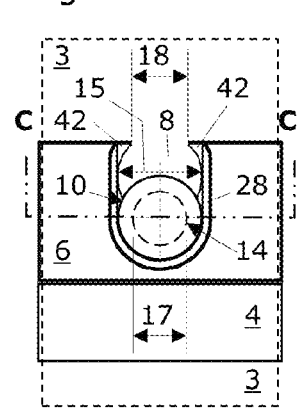
Figure 7A:
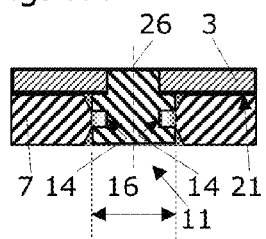
Figure 7B:
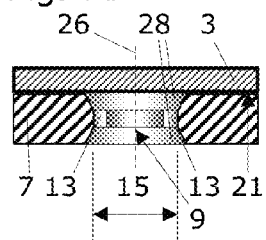
Figure 7C:
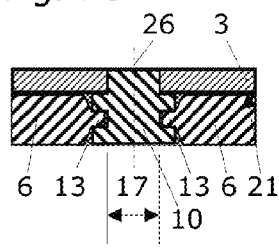
Figure 8A:
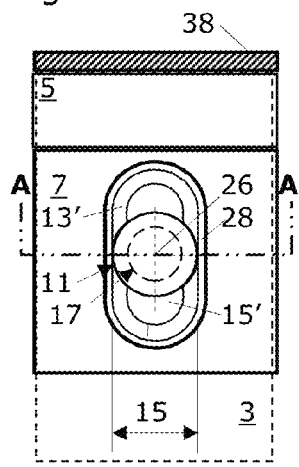
Figure 8B:
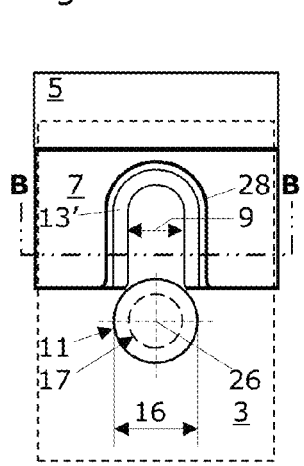
Figure 8C:
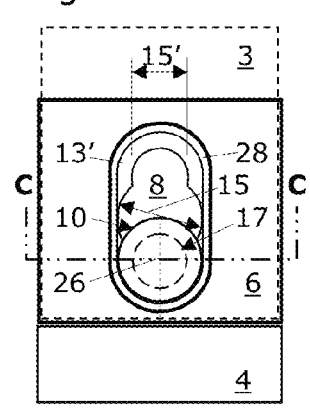
Figure 9A:
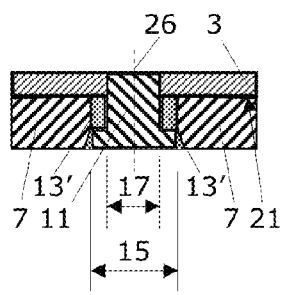
Figure 9B:
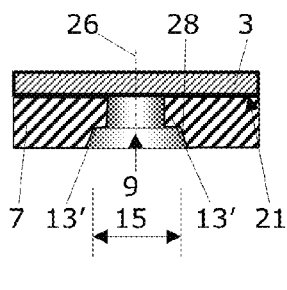
Figure 9C:
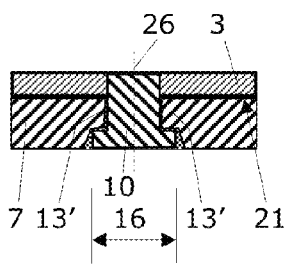
Figure 10A:
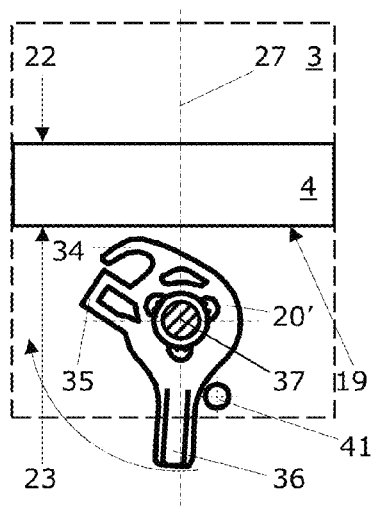

FIG. 5A showing a vertical section through the upper part of the front frame part having detent rail, stop surface, and tabletop element having clamping lever, and FIG. 5B showing a vertical section through the upper part of the rear frame part having detent rail and detent bolt;

FIG. 6 shows detail views of a detent rail/detent bolt combination according to a first embodiment variant:

FIG. 6A showing the detent bolt upon countersinking into the rear upper detent rail during the installation of the tabletop element, FIG. 6B showing the detent bolt in a fixing position in the rear upper detent rail, in which it is fixed, and FIG. 6C showing the detent bolt in an end position in which it is fixed blocked in the front upper detent rail;

FIG. 7 shows detail sections through the detent rail/detent bolt combination according to the first embodiment variant of FIG. 6:

FIG. 7A showing the detent bolt placed in the recess of the detent rail during the installation of the tabletop element, FIG. 7B showing the detent opening behind the detent bolt, and FIG. 7C showing the detent bolt in an end position in which it is fixed blocked in the front upper detent rail;

FIG. 8 shows detail views of a detent rail/detent bolt combination according to a second and third embodiment variant:

FIG. 8A showing the detent bolt upon countersinking in the rear upper detent rail according to a second embodiment variant during the installation of the tabletop element, FIG. 8B showing the detent bolt upon insertion into the rear upper detent rail according to a third embodiment variant during the installation of the tabletop element, and FIG. 8C showing the detent bolt in an end position, in which it is fixed blocked in the front upper detent rail according to a second embodiment variant;

FIG. 9 shows detail sections through the detent rail/detent bolt interaction according to the second and third embodiment variants of FIG. 8:

FIG. 9A showing the detent bolt placed in the recess of the detent rail during the installation of the tabletop element, FIG. 9B showing the detent opening behind the detent bolt, and FIG. 9C showing the detent bolt in an end position, in which it is fixed blocked in the front upper detent rail;

FIG. 10 shows detail views of a clamping lever/stop surface interaction in the upper tabletop level:

FIG. 10A showing the clamping lever in the open position, and

Figure 10B:
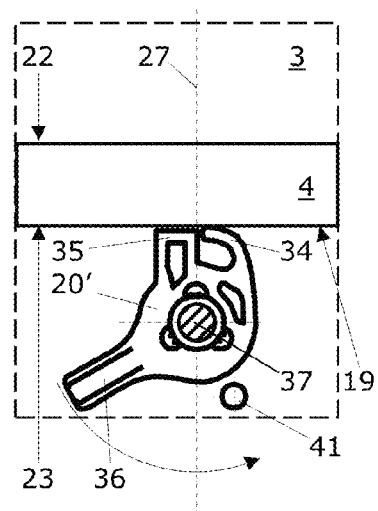
Figure 11A:
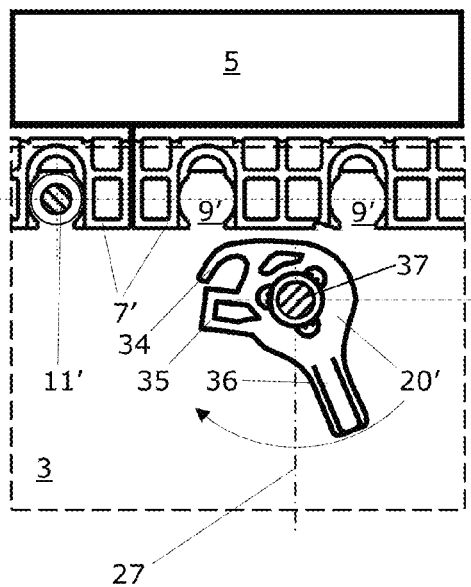

FIG. 10B showing the clamping lever in the locked position;

FIG. 11 shows detail views of a clamping lever/detent rail interaction in the lower tabletop level:

FIG. 11A showing the clamping lever in the open position, and

Figure 11B:
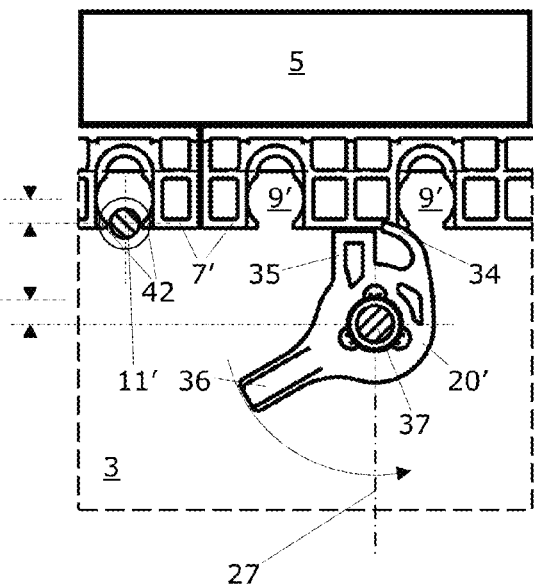
Figure 12A:
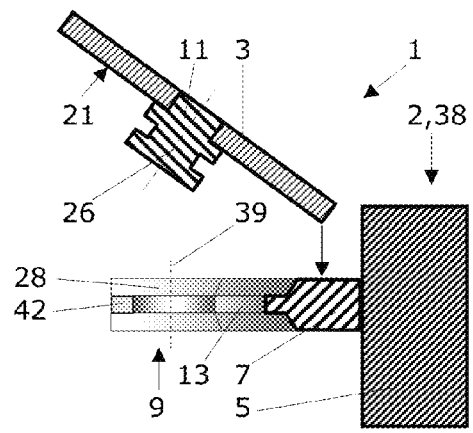
Figure 12B:
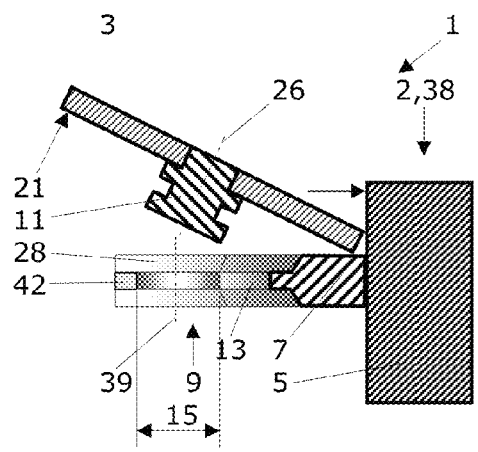
Figure 12C:
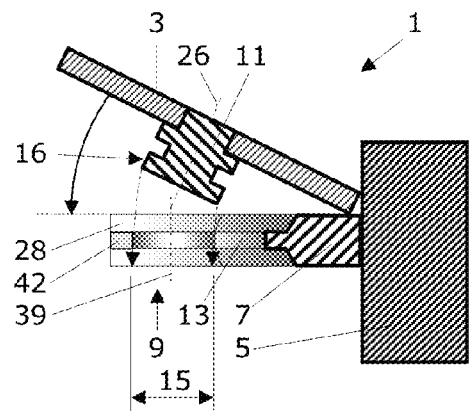
Figure 12D:
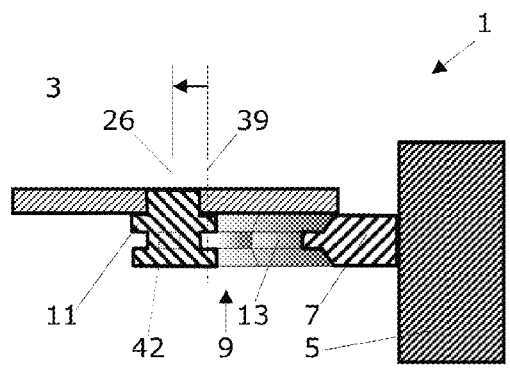
Figure 12E:
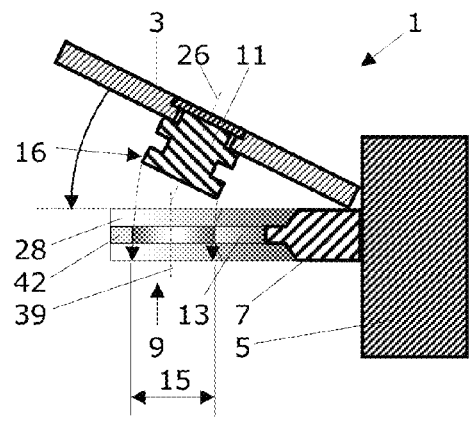
Figure 12F:
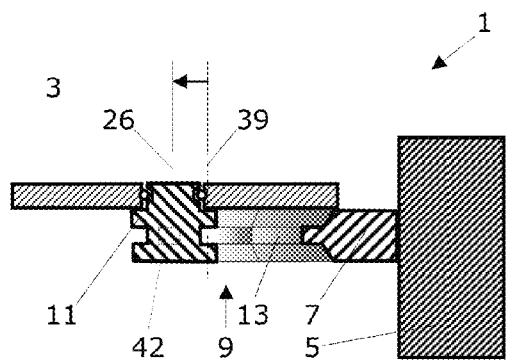

FIG. 11B showing the clamping lever in the locked position;

FIG. 12 shows detail views through a rear detent rail upon installation of the tabletop element:

FIG. 12A showing the first step of inlaying a tabletop element with application of a detent bolt to the rear detent rail according to a first embodiment;

FIG. 12B shows the second step of inlaying the tabletop element with additional application of the detent bolt to a rear stop according to the first embodiment;

FIG. 12C shows the third step of inlaying the tabletop element with pivoting into the horizontal while simultaneously applying the detent bolt to the rear detent rail and the rear stop according to the first embodiment;

FIG. 12D shows the fourth step of inlaying the tabletop element with horizontal displacement and fixing of the tabletop element using the detent bolt according to the first embodiment;

FIG. 12E shows the third step of inlaying the tabletop element with pivoting into the horizontal while simultaneously applying a detent bolt to the rear detent rail and the rear stop according to a second embodiment; and FIG. 12F shows the fourth step of inlaying the tabletop element with horizontal displacement and fixing of the tabletop element using a detent bolt according to a third embodiment.

DETAILED DESCRIPTION OF THE PRESENT INVENTION

Figure 1:
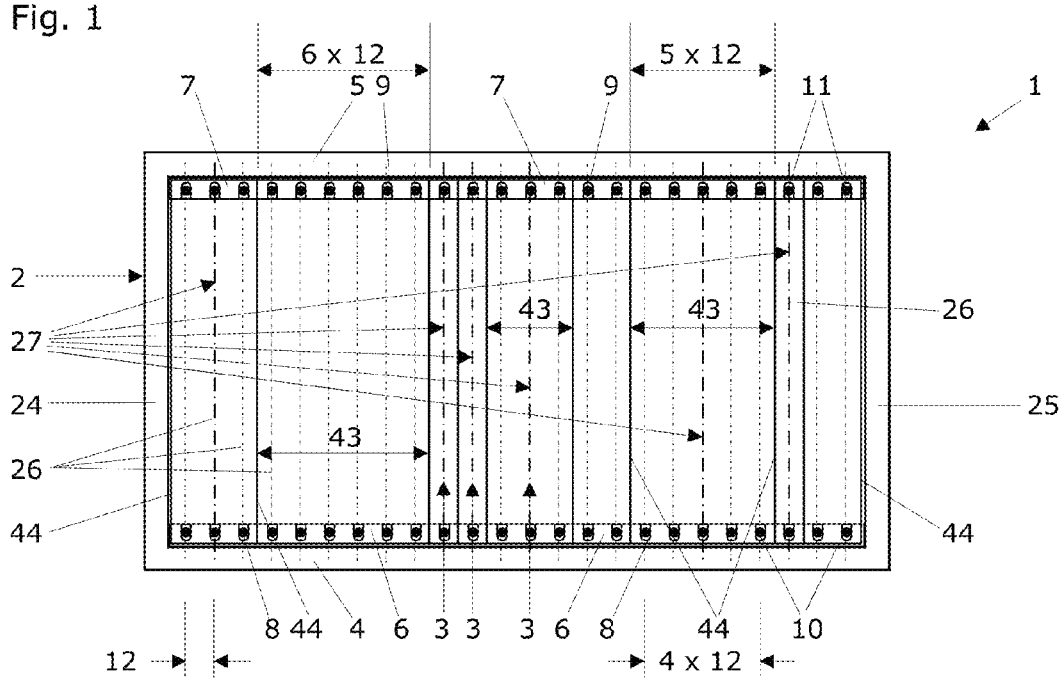
FIG. 1 shows a top view of a laboratory table according to a first embodiment having a number of tabletop elements installed in an intermediate space of the frame.

FIG. 1 shows a top view of a laboratory table 1 according to a first embodiment having a number of tabletop elements 3 installed in an intermediate space of the frame 2. This laboratory table 1 comprises at least one frame 2 having a front frame part and a rear frame part 4,5 opposite thereto as well as tabletop elements 3 positionable on this at least one frame 2. The frame parts 4,5 arranged opposite to one another are preferably arranged parallel to one another and it is also preferable for the frame 2 to comprise two further frame parts 24,25 and to be implemented as a rectangular frame. The tabletop elements 3 of the laboratory table 1 are preferably smaller in at least one horizontal dimension than the frame 2 according to a first embodiment. Tabletop elements 3 of the laboratory table 1 according to a first embodiment, which are smaller in all horizontal dimensions than the frame 2, are also preferred. In addition, the following variants of the arrangement of the tabletop elements in relation to the frame supporting these tabletop elements are preferable as needed:

- the tabletop elements are located at a higher level than the uppermost frame surface;
- the surface of the tabletop elements is flush with the uppermost frame surface;
- the tabletop elements are located at a lower level than the uppermost frame surface.

In particular the first-mentioned variant allows the provision of a laboratory table 1 having a completely flat surface.

In addition, it can be provided for smaller laboratory devices that the frame is smaller than the individual tabletop element, which can protrude beyond the frame on at least one side or also on all sides. Replaceable tabletop elements can also be used in the case of simple laboratory devices. These tabletop elements can comprise very special equipment and/ or structures, so that the work surface of these simple laboratory devices can be assigned permanently or also only temporarily to specific workflows. The frame 2 comprises at least one detent rail 6,7, which is arranged on the front or rear frame part 4,5, having detent openings 8,9. Each of these detent openings 8, 9 is implemented and arranged for the insertion and for the sliding guiding of a detent bolt 10, 11 of a tabletop element 3. The sliding direction of the detent bolt is preferably horizontal.

The tabletop elements 3, which are shown transparent here, comprise at least one detent bolt 10,11, which is implemented and arranged for the insertion and for the sliding guiding in one of the detent openings 8,9 of these detent rails 6,7. At least a part of these detent openings 8, 9 is preferably implemented for fixing a corresponding detent bolt 10, 11 of a tabletop element 3 in a vertical direction. The detent rails 6,7 shown here are implemented as laterally open in the area of the detent openings 8,9. The detent openings 8,9 of the detent rails 6,7 are arranged at a regular, modular distance 12. The detent bolts 10,11 of tabletop elements 3 having at least two front or rear detent bolts 10,11 are preferably arranged at the same distance 12 or a multiple of this distance 12.

The tabletop elements 3 can have uniform or differing widths 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 1, tabletop elements 3 are implemented having a width 43 which (viewed from left to right) corresponds to approximately triple, sixfold (6×12), single, single, triple, double, fivefold (5×12), single, and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3.

Thus, it is obvious in FIG. 1, for example, that the third tabletop element 3 from the right is equipped with five rear detent bolts 11 and with a row of five front detent bolts 10, the detent bolts 10,11 being arranged four times at equal distance 12 in each of these two rows. Furthermore, it is obvious from FIG. 1 that in the second tabletop element 3 from the right, which is only equipped with one front and one rear detent bolt 10,11, the bolt axis 26 is identical to the plate axis 27. In contrast, in the first tabletop element 3 from the left, which is equipped with three front and three rear detent bolts 10,11, only the middle bolt axis 26 is identical to the plate axis 27.

Figure 2:
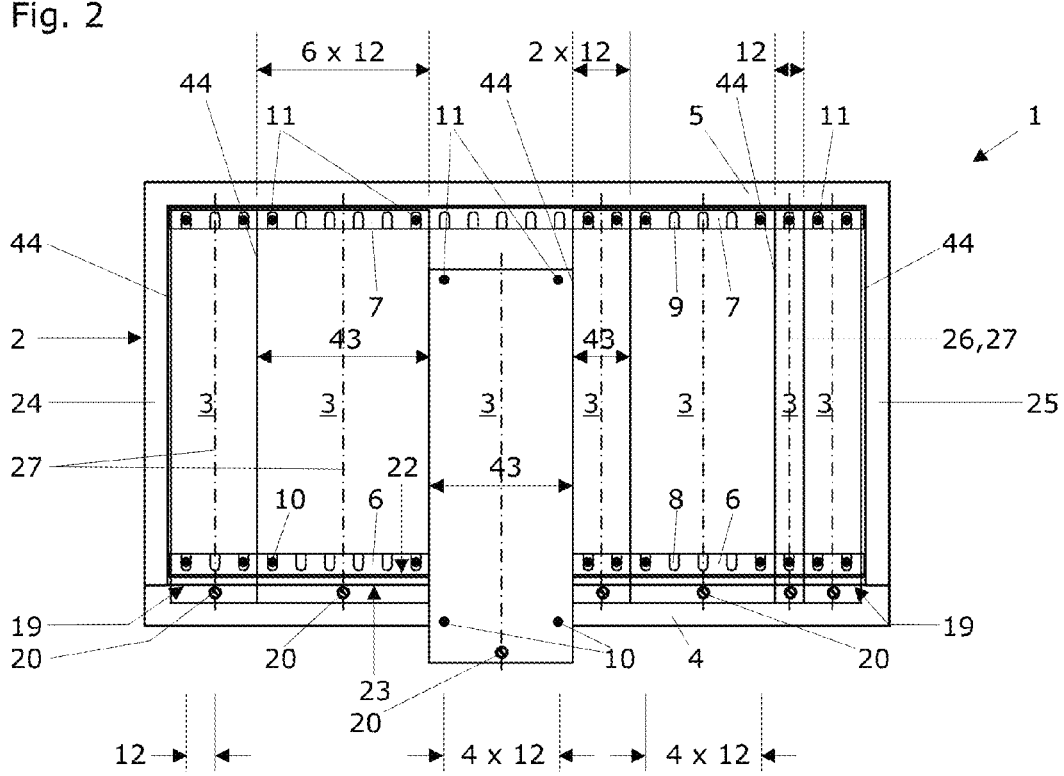
FIG. 2 shows a top view of a laboratory table according to a second embodiment having a number of tabletop elements, which are partially installed in an intermediate space of the frame and partially protrude beyond the frame.

FIG. 2 shows a top view of a laboratory table 1 according to a second embodiment having a number of tabletop elements 3 which are partially installed in an intermediate space of the frame 2 and partially protrude beyond the frame 2. In this second embodiment, all frame parts 4,5 and 24,25 are not actually at the same height as in the first embodiment: The front frame part 4 is somewhat lowered and the installed tabletop elements 3 partially protrude beyond it. Therefore, the frame part 4 is arranged lying lower in relation to the frame part 5 arranged opposite thereto here.

One of the tabletop elements 3, which are shown transparent here, is removed from the frame and in spite of its size, which would offer space for a row of five rear detent bolts 11 and for a row of five front detent bolts 10, only has two front and two rear detent bolts 10,11. However, these four detent bolts 10,11 are arranged so that they correspond to the modular grid of the detent rails 6,7 having the uniform distance 12. The four detent bolts 10,11 are arranged at the points which are as far as possible away from one another; the greatest possible stability of this tabletop element 3 is therefore achieved.

The tabletop elements 3 can have a uniform or differing width 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 2, tabletop elements 3 are implemented having a width 43 which (viewed from left to right) corresponds to approximately triple, sixfold (6×12), fivefold, double (2×12), fivefold, single (12), and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3.

In FIG. 2, all tabletop elements 3 were equipped with at least two, but preferably with four detent bolts 10,11 according to this principle of the greatest possible stability. In the laboratory table 1 shown here, the frame 2 comprises a stop surface 19, which is arranged on the front of the frame parts 4,5 located opposite to one another. This stop surface 19 is implemented here as a vertical upright web on the frame part 4.

All of the tabletop elements 3 shown in FIG. 2 additionally comprise a fixing mechanism 20 arranged on a lower side 21 of the tabletop elements 3. This fixing mechanism 20 is implemented as pivotable around an axis 37 toward the stop surface 19 during the installation of the tabletop elements 3 (cf. FIG. 5A). In the example shown in FIG. 2, the fixing mechanism 20 of the tabletop elements 3 is implemented as a clamping lever 20' (cf. FIG. 10). This clamping lever 20' comprises a handle 36, a fixing block 35, and a clamping bow 34. The fixing block 35 defines a closure location of the clamping lever 20'. The clamping bow 34 is applied to the stop surface 19 in a springy manner in this closure location of the clamping lever 20' and exerts a spring force on the stop surface 19 (cf. FIG. 10B).

Figure 3:
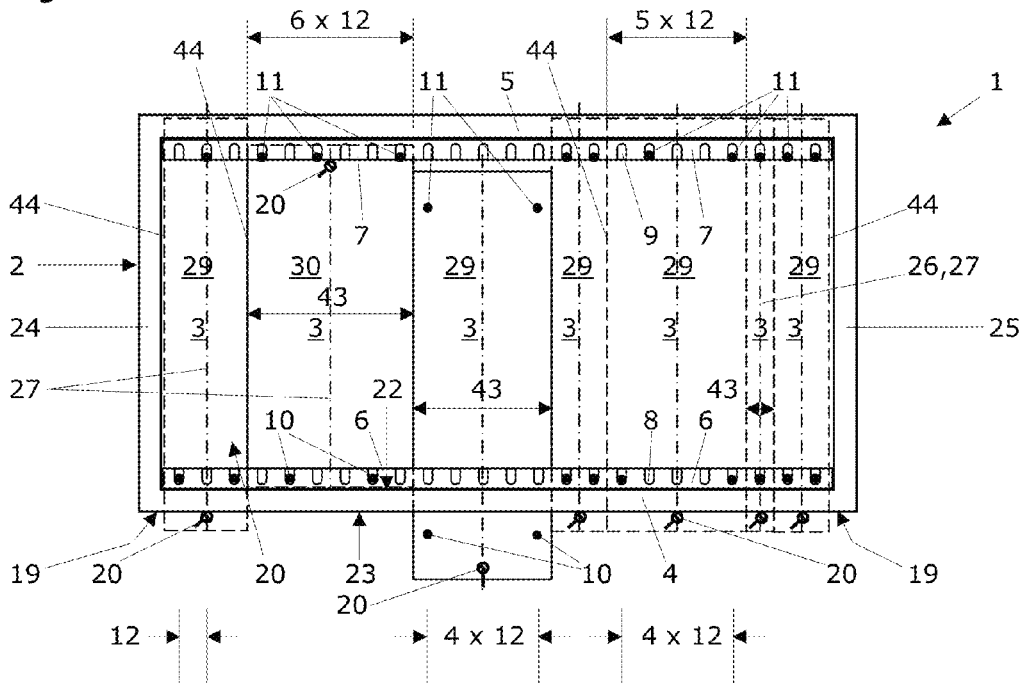
FIG. 3 shows a bottom view of a laboratory table according to a third embodiment having a tabletop element, which is installed in an intermediate space of the frame, of a lower tabletop level and having a number of tabletop elements, which at least partially protrude beyond the frame on both sides, of an upper tabletop level.

FIG. 3 shows a bottom view of a laboratory table 1 according to a third embodiment having a tabletop element 3, which is installed in an intermediate space of the frame 2, of a lower tabletop level 30, and having a number of tabletop elements 3, which at least partially protrude beyond the frame 2 on both sides, of an upper tabletop level 29. In this embodiment shown here, the installed tabletop elements 3 of the upper tabletop level 29 protrude beyond the front frame part 4 and the stop surface 19 on the front frame part 4 (cf. first tabletop element 3 from the left and the four tabletop elements 3 from the right).

This laboratory table 1 comprises at least one frame 2 having a front frame part and a rear frame part 4,5 opposite thereto as well as tabletop elements 3 positionable on this at least one frame 2. The frame 2 comprises at least one detent rail 6,6',7,7', which is positioned on the front or rear frame part 4,5, having detent openings 8,8',9,9'. Each of these detent openings 8,8',9,9' is implemented and arranged for the insertion and for the sliding guiding of a detent bolt 10,11 of a tabletop element 3. The tabletop elements 3 of this laboratory table 1 comprise at least one detent bolt 10,11, which is implemented and arranged for the insertion and for the sliding guiding in one of the detent openings 8,8',9,9' of these detent rails 6,6',7,7'. The sliding direction of the detent bolts 10,11 is preferably horizontal.

In this laboratory table 1, the tabletop elements 3 of the upper tabletop level 29 are only smaller in one horizontal dimension than the frame 2. In contrast, the tabletop elements 3 of the lower tabletop level 30 are smaller in both horizontal dimensions than the frame 2. At least a part, but preferably all of these detent openings 8,8',9,9' are implemented for fixing a detent bolt 10,11 of a tabletop element 3 in a vertical direction. The detent rails 6,6',7,7' are implemented as laterally open in the area of the detent openings 8,8',9,9' here (cf. also FIG. 6). Notwithstanding this illustration, the detent rails 6,6',7,7' can also be implemented as laterally closed in the area of the detent openings 8,8',9,9' (cf. FIGS. 8A and 8C).

The detent openings 8,9 of the detent rails 6,7 are preferably arranged at a regular distance 12, in a so-called grid. The detent bolts 10,11 of tabletop elements 3 having at least two front or rear detent bolts 10,11 are preferably arranged at the same modular distance 12 or at a multiple of this distance 12. Depending on the provided load of a tabletop element 3, the detent bolts 10,11 (as shown in FIG. 3) can be arranged arbitrarily in position and number and nonetheless following the modular grid dimension defined by the distance 12. The detent rails 6,6',7,7' are preferably fastened on the frame parts 4,5 opposite to one another so that the detent openings 8,8', 9,9' of the two detent rails 6,6',7,7' are oriented toward one another.

The tabletop elements 3 can have a uniform or differing width 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 3, tabletop elements 3 are shown having a width 43 which (viewed from left to right) corresponds to approximately triple, sixfold (6×12), fivefold, double, fivefold (5×12), single, and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3.

Figure 4:
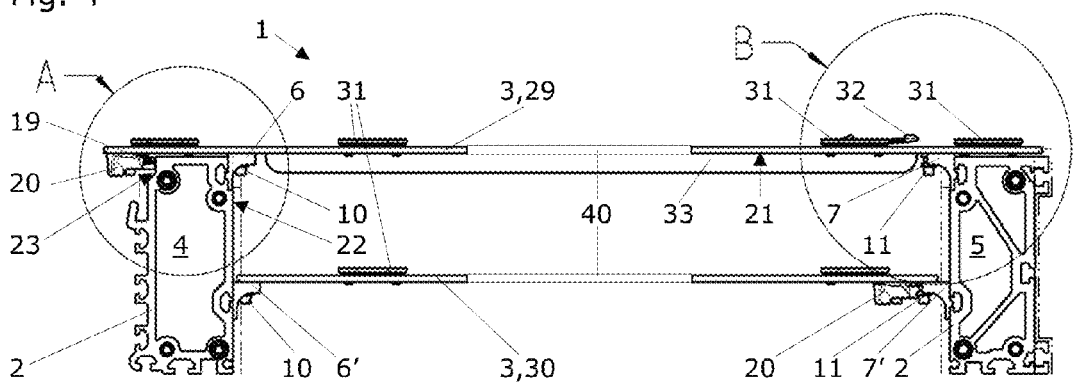
FIG. 4 shows a vertical cross section through the front frame part and the rear frame part of the laboratory table frame having one tabletop element installed in the lower tabletop level and one tabletop element installed in the upper tabletop level.

The laboratory table 1 according to the third embodiment preferably comprises tabletop elements 3 in an upper tabletop level 29 and in a lower tabletop level 30, which are aligned essentially horizontally in the installed state (cf. FIGS. 3 and 4). In addition, the frame parts 4,5 arranged opposite to one another are preferably arranged parallel to one another and the frame 2 preferably comprises two further frame parts 24,25 and is implemented as a rectangular frame. The laboratory table 1 according to the third embodiment can also comprise tabletop elements 3 only in an upper tabletop level 29 or only in a lower tabletop level 30, which are aligned essentially horizontally in the installed state. One tabletop element 3 is preferably arranged either in the upper tabletop level 29 or in the lower tabletop level 30 respectively at one position of the laboratory table 1.

All tabletop elements 3 shown up to this point additionally comprise at least one fixing mechanism 20, which is preferably arranged on a lower side 21 of the tabletop elements 3. This fixing mechanism 20 is implemented as pivotable toward the stop surface 19 around an axis 37 upon installation of the tabletop elements 3. In the example shown in FIG. 3, the fixing mechanism 20 of the tabletop elements 3 is implemented as a clamping lever 20' (cf. FIG. 10). This clamping lever 20' comprises a handle 36, a fixing block 35, and a clamping bow 34. The fixing block 35 defines a closure location of the clamping lever 20'.

In the tabletop elements 3 of the upper tabletop level 29, the clamping lever 20' is preferably arranged in the front area (close to an operator) of a laboratory table 1, so that the clamping lever 20' can be easily moved manually by the operator. The clamping bow 34 is applied in a springy manner in the closure location of the clamping lever 20' to the stop surface 19 and exerts a spring force on the stop surface 19 (cf. FIG. 10B).

In the tabletop elements 3 of the lower tabletop level 30, the clamping lever 20' is preferably arranged in the rear area (distant from an operator) of the laboratory table 1. Nonetheless (or particularly because of this), the clamping lever 20' can be easily moved manually by the operator. The clamping bow 34 is applied in a springy manner in the closure location of the clamping lever 20' to the detent rail 7' and exerts a spring force on the detent rail 7' (cf. FIG. 11B). Notwithstanding this illustration, in the tabletop elements 3 of the lower tabletop level 30, the clamping lever 20' can be arranged in the front area (close to an operator) of the laboratory table 1. Preferably, only a few tabletop elements 3 are arranged in the lower tabletop level 30, so that as few clamping levers 20' as possible can contribute to a deformation of the frame 2.

In all of the embodiments of the laboratory table 1 according to the present invention shown up to this point, the detent bolts 10,11 are arranged on the lower side 21 of the tabletop elements 3. Notwithstanding this illustration, the detent bolts 10,11 can also be arranged on the upper side of the tabletop elements 3, so that the tabletop elements 3 could be fastened from below on the detent rails 6,6',7,7' (not preferred and not shown).

In all of the embodiments shown up to this point of the laboratory table 1 according to the invention, the detent rails 6,6',7,7' are fastened on the frame parts 4,5 opposite to one another, so that the detent openings 8,8',9,9' of the two detent rails 6,6',7,7' are oriented toward one another. The detent rails 6,6',7,7' are therefore preferably arranged on the table inner side of the frame.

Notwithstanding these illustrations in FIGS. 1 to 3, the detent rails 6,6',7,7' can be fastened on the frame parts 4,5 opposite to another so that the detent openings 8,8',9,9' of the two detent rails 6,6',7,7' are oriented away from one another. The detent rails 6,6',7,7' are then preferably arranged on the table outer side of the frame (not shown).

Also notwithstanding these illustrations in FIGS. 1 to 3, the detent rails 6,6',7,7' can also be fastened on the frame parts 4,5 opposite to one another, so that the detent openings 8,8',9,9' of the two detent rails 6,6',7,7' are oriented in the same direction. The detent rails 6,6',7,7' are then preferably arranged either on the table inner side or on the table outer side of the frame (not shown).

FIG. 4 shows a vertical cross section through the front frame part 4 (marked by A) and through the rear frame part 5 (marked by B) of the frame 2 of the laboratory table 1 according to the invention having a tabletop element 3 installed in the lower tabletop level 30 and a tabletop element 3 installed in the upper tabletop level 29 (cf. also FIG. 3). The tabletop elements 3 in the upper tabletop level 29 and/or in the lower tabletop level 30 are preferably aligned essentially horizontally in the installed state.

Cutouts 40 are additionally shown in FIG. 4. One such cutout 40 is applied in a tabletop element 3 arranged at this position of the laboratory table 1, i.e., either in the upper tabletop level 29 or in the lower tabletop level 30. Through this cutout 40, components having taller installation height can be installed on a lower secondary working level in laboratory facilities, so that the movement range of the robots present in these laboratory facilities is impaired substantially less. Alternatively or additionally thereto, such cutouts 40 in tabletop elements 3 of the work surface of laboratory devices or laboratory facilities allow the reaching through or transfer of containers (e.g., for loading/unloading a centrifuge) through the work surface.

As shown in the circle A, the frame 2 comprises a stop surface 19, which is arranged here on the front of the frame parts 4 opposite to one another. This stop surface 19 is an outer surface of the frame part 4 or preferably a milled notch on the frame part 4 here. Very generally, a frame 2 can comprise a stop surface 19, which is arranged on the front or rear of the frame parts 4,5 opposite to one another. In addition, this stop surface 19 can be selected by a person skilled in the art from the group of stop surfaces 19 which comprises an outer surface of a frame part 4,5; a milled notch on a frame part 4,5; a vertical upright web on a frame part 4,5 (cf. FIG. 2), a web protruding horizontally beyond a frame part 4,5, and arbitrary combinations of these stop surfaces 19.

In this exemplary embodiment (cf. also FIG. 3), the installed tabletop elements 3 of the upper tabletop level 29 protrude horizontally beyond the front frame part 4 and the stop surface 19 on the front frame part 4 and the installed tabletop elements 3 of the lower tabletop level 30 laterally approach the frame parts 4,5 arranged opposite to one another. The tabletop elements 3 comprise at least one fixing mechanism 20 arranged on a lower side 21 of the tabletop elements 3, which is implemented as pivotable around an axis 37 toward the stop surface 19 or toward one of the detent rails 6',7' upon installation of the tabletop elements 3.

FIG. 5 shows detail sections of FIG. 4:

FIG. 5A shows a vertical section through the upper part of the frame 2, i.e., the front frame part 4 having detent rail 6, a stop surface 19, and a tabletop element 3 having clamping lever 20'. This clamping lever 20' is used here as a fixing mechanism 20, which is arranged on a lower side 21 of the tabletop element 3. To fix the installed tabletop element 3, this clamping lever 20' was pivoted around an axis 37 toward the stop surface 19. A clamping bow 34 is thus applied in a closure location, which is defined by a fixing block 35 of the clamping lever 20', in a springy manner to the stop surface 19 and exerts a spring force on the stop surface 19 (cf. FIG. 10B). Through the fixing, the detent bolt 10 is drawn into its end position in the detent rail 6 (cf. FIG. 6C); the frame part 4 having the stop surface 19 is clamped between the combination detent rail 6/detent bolt 10 and the clamping bow 34 of the clamping lever 20'. Blocked fixing of the detent bolt 10,11 thus results. The sliding direction of the detent bolt 10,11 is preferably horizontal.

FIG. 5B shows a vertical section through the upper part of the frame 2, i.e., the rear frame part 5 having detent rail 7 and detent bolt 11. The detent bolt 11 is drawn into its fixed position in the detent rail 7 by the fixing of the tabletop element 3 and fixed therein in relation to movements in the vertical direction (cf. FIG. 6B), in that the holding portions 42 of the detent rail 7 engage in the groove 14 of the detent bolt 11. The displacement of the tabletop element 3 by the fixing results in a distance d between the rear end of the tabletop element 3 and the front edge of a preferably attached vertical rear wall 38.

Reinforcement brackets 33 are preferably provided on the lower side 21 of the tabletop element 3, which increase the stability of the tabletop element 3 and contribute to minimizing the weight of the tabletop element 3. Holding rails 31 are preferably provided on the upper side of the tabletop element 3, which are used for the purpose of exactly positioning arbitrary objects (e.g., so-called "carriers" for microplates, liquid containers, so-called "racks" fur sample tubes, etc.) on the worktable defined by the tabletop elements 3. At least one of these holding rails 31, which fixes the objects in a defined manner in a horizontal x-ray direction, preferably comprises a detent cam 32, which also fixes this object in the horizontal Y direction extending perpendicularly thereto in a defined manner.

FIG. 6 shows detail views of a detent rail/detent bolt combination according to a first embodiment variant, which is characterized in that the detent rails 6,6',7,7' are implemented as laterally open in the area of the detent openings 8,8',9,9', a holding web 13 is arranged in the detent openings 8,8',9,9' of the detent rails 6,6',7,7', and the detent bolts 10,11 have a circular cross section and comprise a peripheral groove 14, whose width is adapted to the height of the first holding web 13 in the detent openings 8,8',9,9' of the detent rails 6,6',7,7'.

Notwithstanding this definition, the detent bolts 10,11 can also have a shape which deviates from the preferred cylindrical shape. The detent bolts can thus, for example, have an oval, elliptical, or polygonal cross section (with or without rounded corners). In addition, the groove 14 does not have to be implemented as peripheral. The groove 14 can also only be located on those sides of the detent bolts 10,11 which extend parallel to the guide direction (Y direction) of the holding webs 13, which also only extend in the Y direction.

As a further alternative embodiment of the detent bolts 10,11, it can be provided that the detent bolts 10,11 have a continuously uniform cross section (not shown) and therefore can be designated as a "pin". Such "pins" do not provide any hold of the tabletop elements 3 in the vertical Z direction, however, because they also do not engage below possibly provided first or second holding webs 13,13'. However, it can be entirely sufficient for the stability of the tabletop to only provide a pin and no detent bolt 10,11 on the side of a tabletop element 3 on which the clamping mechanism 20 is arranged; in such a case, a detent bolt 10,11 would only be provided on the side of the tabletop element 3 opposite to the fixing mechanism 20, because on one side the clamping using the fixing mechanism 20 can already cause sufficient securing for the tabletop elements 3. This is the case above all if no objects (e.g., pipette tips or microplates) must be received by these tabletop elements 3 against the resistance of a holding mechanism arranged on these tabletop elements 3 or against another resistance. If only "pins" are used as the detent bolts 10,11, the arrangement of holding webs 13,13' can be omitted; however (to improve the adhesion of the tabletop elements 3 on the frame 2), it can be provided that a fixing mechanism 20 is arranged in each case on both sides of the tabletop element 3. As shown, depending on the need and the given conditions, the provision of an arbitrary combination and number of detent bolts 10,11 and/or "pins" and fixing mechanisms 20 is possible.

FIG. 6A shows the detent bolt 11 upon countersinking in the rear upper detent rail 7 during the installation of the tabletop element 3. The tabletop element 3 preferably protrudes beyond the rear frame part 5 and more preferably touches the front side of a rear wall 38. This detent bolt 11 (having the bolt axis 26) plunges into a recess 15 in the detent opening 9, the diameter of the recess 15 being somewhat larger than the largest cross section 16 of the detent bolt 11. Infeed chamfers on both flanks of the detent opening 9 make it easier to center and therefore insert the detent bolt 11 into the recess 15. The letters A-A identify the section line of the illustration in FIG. 7A. The holding portions 42 of the first holding web 13 are well visible here and are not concealed by the detent bolt 11.

FIG. 6B shows the detent bolt 11 in a fixing position in the rear upper detent rail 7, the detent bolt 11 (having the bolt axis 26) being fixed in this fixing position in the horizontal X direction so that it is fixed in the Z direction. This is preferably produced in that the holding webs 13 in the detent openings 9 of the detent rail 7 are implemented as open on one side in the horizontal direction, and the holding webs 13 in the detent openings 9 of the detent rails 7 for vertically fixing and horizontally guiding the detent bolt 11 each have a constriction 18 on their open side, which is wider than a reduced cross section 17 of the detent bolt 11 in the area of the groove 14, but is narrower than the largest cross section 16 of the detent bolt 11. Through the holding portions 42 (shown by dashed lines here, because they are largely concealed by the detent bolt 11), which are arranged on the constriction 18, of the holding webs 13, which engage in the groove 14 of the detent bolt 11, this detent bolt 11 is prevented from moving in the Z direction. The letters B-B identify the section line of the illustration in FIG. 7B. The detent bolt 11 is simultaneously guided in the horizontal direction by the two holding portions 42 spaced apart by the constriction 18 (cf. FIG. 6C). The two holding portions 42 practically touch the base of the groove 14 in the detent bolt 11 and guide it in the horizontal direction, so that this detent bolt 11 cannot deviate in the longitudinal direction of the rear frame part 5.

FIG. 6C shows the detent bolt 10 in an end position, in which it is fixed blocked in the front upper detent rail 6. In this position of the detent bolt 10, the holding web 13 in the detent opening 8 of the detent rail 6 engages in the groove 14 in the detent bolt 11 and fixes it in the vertical direction and parallel to the longitudinal direction of the front frame part 4. The detent openings 8 of the detent rail 6 each have a constriction 18 on their open side for vertically fixing and horizontally guiding the detent bolt 11. If the detent bolt 10 has a rectangular cross section, notwithstanding the illustrations in FIG. 6, for example, and only comprises a groove 14 on the two sides which extend parallel to the guide direction (Y direction) of holding webs 13 also only extending in the Y direction, the detent bolt 11 is located in its end position having one side on the detent rail 6 which does not have a groove 14. Correspondingly, the detent rail 6 also could not have a holding web 13 at this point of the detent opening 8. The letters C-C identify the section line of the illustration in FIG. 7C. The holding portions 42 of the first holding web 13 are well visible here and are not concealed by the detent bolt 11.

FIG. 7 shows detail sections through the detent rail/detent bolt combination according to the first embodiment variant of FIG. 6. As shown, the detent bolt 11 is preferably implemented as cylindrical, this allows more cost-effective manufacturing. The detent bolt 11 preferably has, on its rear end, a cylindrical constriction, using which it is fastened in a correspondingly dimensioned hole of the tabletop element 3. Preferred fastenings of the detent bolts 10,11 in the tabletop elements 3 comprise, for example, the use of a press fit and/or adhesives.

FIG. 7A shows the detent bolt 11 (having the bolt axis 26) placed in the recess 15 of the detent rail 7 during the installation of the tabletop element 3. The largest cross section 16 of this detent bolt 11 is, of course, smaller than the diameter of the recess 15, which is free of holding webs 13, which could engage in the groove 14 of the detent bolt 11. The letters A-A identify the section line of the illustration in FIG. 9A.

FIG. 7B shows the detent opening 9 behind the detent bolt 11. It is clear here that the recess 15 does not have holding webs 13. Holding webs 13 are therefore only shown in the horizontal projection here, but not in section. The detent rail 7 preferably has infeed chamfers 28, which make it easier to correctly position the detent bolt 11 in the detent opening 9 of the detent rail 7. The letters B-B identify the section line of the illustration in FIG. 9B.

FIG. 7C shows the detent bolt 10 in an end position, in which it is fixed blocked in the front upper detent rail 6. It is clear here that the holding webs 13 engage in the groove 14 of the detent bolt 10, but the reduced cross section 17 of the detent bolt 10 is somewhat smaller than the opening of the oblong hole 15' between the holding webs 13. The letters C-C identify the section line of the illustration in FIG. 9C.

FIG. 8 shows detail views of a detent rail/detent bolt combination according to a second and third embodiment variant. The second and third embodiment variants also differ from the first embodiment variant, inter alia, in that the first holding web 13 (according to the first embodiment variant) is relatively narrow and engages in a groove 14 on a detent bolt 10,11, which essentially has the cross-sectional shape of a "recumbent H". In contrast, the detent bolt 10,11 in the second and third embodiment variants has a cross-sectional shape which essentially corresponds to an "upside-down T".

The second embodiment variant is characterized in that the detent rails 6,6',7,7' are implemented as laterally closed in the area of the detent openings 8,8',9,9', a second holding web 13' is arranged in the detent openings 8,8',9,9' of the detent rails 6,6',7,7', and the detent bolts 10,11 have a circular cross section and comprise a reduced cross section 17, whose width is adapted to the height of the second holding web 13' in the detent openings 8,8',9,9' of the detent rails 6,6',7,7'. As shown, the second embodiment variant of the detent rails 6,6',7,7' comprises a recess 15, which is arranged approximately in the middle of the detent openings 8,8',9,9'.

The third embodiment variant is characterized in that the detent rails 6,6',7,7' are implemented as laterally open in the area of the detent openings 8,8',9,9', a second holding web 13' is arranged in the detent openings 8,8',9,9' of the detent rails 6,6',7,7', and the detent bolts 10, 11 have a circular cross section and comprise a reduced cross section 17, whose width is adapted to the height of the second holding web 13' in the detent openings 8,8',9,9' of the detent rails 6,6',7,7'. As shown, in comparison to the second embodiment variant, the third embodiment variant of the detent rails 6,6',7,7' does not comprise a recess 15.

FIG. 8A shows the detent bolt 11 (having the bolt axis 26) upon countersinking in the rear upper detent rail 7 according to a second embodiment variant during the installation of the tabletop element 3. The tabletop element 3 preferably protrudes beyond the rear frame part 9 and more preferably touches the front side of a rear wall 38. The largest cross section 16 of this detent bolt 11 is, of course, smaller than the diameter of the recess 15, which is free of holding webs 13', which could engage in the reduced cross section 17 of the detent bolt 11. The detent rail 7 preferably has infeed chamfers 28, which make it easier to correctly position the detent bolt 11 in the detent opening 9 of the detent rail 7 of the second embodiment variant.

FIG. 8B shows the detent bolt 11 (having the bolt axis 26) upon insertion into the rear upper detent rail 7 of the third embodiment variant during the installation of the tabletop element 3.

FIG. 8C shows the detent bolt 10 (having the bolt axis 26) in an end position, in which it is fixed blocked in the front upper detent rail 6 of the second embodiment variant.

FIG. 9 shows detail sections through the detent rail/detent bolt interaction according to the second and third embodiment variants of FIG. 8.

FIG. 9A shows the detent bolt 11 (having the bolt axis 26) placed in the recess 15 of the detent rail 7 during the installation of the tabletop element 3. The largest cross section 16 of this detent bolt 11 is, of course, smaller than the diameter of the recess 15, which is free of holding webs 13', which could engage in the reduced cross section 17 of the detent bolt 11.

FIG. 9B shows the detent opening 9 behind the detent bolt 11. The detent rail 7 preferably has infeed chamfers 28, which make it easier to correctly position the detent bolt 11 in the detent opening 9 of the detent rail 7.

FIG. 9C shows the detent bolt 10 in an end position, in which it is fixed blocked in the front upper detent rail 6. It is clear here that the holding webs 13' engage in the reduced cross section 17 of the detent bolt 10, but the reduced cross section 17 of the detent bolt 10 is somewhat smaller than the opening of the oblong hole 15' between the holding webs 13'.

FIG. 10 shows detail views of a clamping lever/stop surface interaction in the upper tabletop level 29 of a laboratory table 1, which comprises at least one frame 2 having a front frame part and a rear frame part 4,5 opposite thereto as well as tabletop elements 3 positionable on this at least one frame 2. The frame 2 comprises a stop surface 19, which is arranged here on the front of the frame parts 4 opposite to one another and is implemented here as a web standing vertically upright beyond the frame part 4. The tabletop element 3 comprises at least one fixing mechanism 20 arranged on its lower side 21, which is implemented as pivotable around an axis 37 toward the stop surface 19 during the installation of the tabletop element 3. This fixing mechanism 20 is shown in FIG. 10A as a clamping lever 20' in the open position.

The at least one fixing mechanism 20 of the tabletop element 3 is implemented here as a clamping lever 20'. This clamping lever 20' comprises a handle 36, a fixing block 35, and a clamping bow 34. The fixing block 35 defines a closure location of the clamping lever 20' in a locked position (cf. FIG. 10B). The clamping bow 34 is applied in a springy manner to the stop surface 19 in this closure location of the clamping lever 20' and exerts a spring force on the stop surface 19.

One practical detail is additionally obvious in FIG. 10: If the clamping lever 20' is not located in the locking position, the handle 36 preferably protrudes visibly beyond the front edge of the tabletop element 3 (cf. FIG. 10A). The handle 36 preferably only disappears below the front edge of the tabletop element 3 when the clamping lever 20' is located in the locked position (cf. FIG. 10B). A simple visual check provides information in this case about whether all tabletop elements 3 have been fixed and locked as prescribed. This arrangement is particularly preferable for the tabletop elements 3 which are arranged in an upper tabletop level 29 (cf. FIGS. 4 and 5).

A further practical detail relates to the so-called over-tightening guard 41 in tabletop elements 3 in the upper tabletop level 29: A bolt is arranged on the lower side 21 of the corresponding tabletop element 3 so that the handle 36 of the clamping lever 20' assumes an end position upon disengagement of the fixing mechanism 20. This end position is selected so that the handle 36 cannot be pivoted too far unintentionally and disappears under the front edge of the tabletop element 3. Such a disappearance could incorrectly be misinterpreted as an indication that the clamping lever 20' is located in the locking position.

FIG. 11 shows detail views of a clamping lever/detent rail interaction in the lower tabletop level 30 of a laboratory table 1 according to the invention, which comprises at least one frame 2 having a front frame part and a rear frame part 4,5 opposite thereto, as well as tabletop elements 3 positionable on this at least one frame 2. The frame 2 has detent rails 6,6',7,7' having detent openings 8,8',9,9'. A lower rear detent rail 7', which is arranged on the rear of the frame parts 5 opposite to one another, is shown here.

The tabletop element 3 comprises at least one fixing mechanism 20 arranged on its lower side 21, which is implemented as pivotable around an axis 37 toward the detent rail 7' upon installation of the tabletop element 3. This fixing mechanism 20 is shown in FIG. 11A as a clamping lever 20' in the open position.

The at least one fixing mechanism 20 of the tabletop element 3 is implemented here as a clamping lever 20'. This clamping lever 20' comprises a handle 36, a fixing block 35, and a clamping bow 34. The fixing block 35 defines a closure location of the clamping lever 20' in a locked position (cf. FIG. 11B). The clamping bow 34 is applied in a springy manner to the detent rail 7' in this closure location of the clamping lever 20' and exerts a spring force on the detent rail 7'

FIG. 12 shows detail sections through a rear upper detent rail 7 during the installation of a tabletop element 3 in the frame 2 of a laboratory table 1 according to the invention. The method carried out in this case for providing a laboratory table 1, which comprises at least one frame 2 having a front frame part and a rear frame part 4,5 opposite thereto as well as tabletop elements 3 positionable on this at least one frame 2, is characterized in that the frame 2 comprises at least one detent rail 6,6',7,7', which is arranged on the front or rear frame part 4,5, having detent openings 8,8',9,9'. Each of these detent openings 8,8',9,9' is implemented and arranged for the insertion and for the sliding guiding of a detent bolt 10,11 of a tabletop element 3. In this method, the tabletop elements 3 are installed using at least one detent bolt 10,11 in this frame 2, in that the at least one detent bolt 10,11 is inserted into one of the detent openings 8,8',9,9' of these detent rails 6,6',7,7' and guided in a sliding manner therein. The sliding direction of the detent bolt 10,11 is preferably horizontal and perpendicular to the longitudinal direction of the rear frame part 5.

FIG. 12A shows the first step of inlaying a tabletop element 3 with application to the rear detent rail 7, which is used as the guide means for reaching the pivot position. The diagonally held tabletop element 3 having the detent bolt 11 fastened captively thereon and its bolt axis 26 are well visible. The upper rear detent opening 9 (having recess axis 39 and infeed chamfers 28) of the upper rear detent rail 7 is also visible, which is ready to receive the detent bolt 11. The detent bolt 11 shown here corresponds to a first embodiment, in which it is immovably fixed by means of a press fit in a corresponding opening in the tabletop element 3.

FIG. 12B shows the second step of inlaying the tabletop element 3 with additional application to a rear stop, this rear stop being able to be provided by a part of the frame 2 or also by the front side of a rear wall 38. The individual parts are the same as in FIG. 12A. In addition, the recess 15 in the detent opening 9 of the detent rail 7 is well visible here. This recess 15 has a cross section which is larger than a largest cross section 16 of the detent bolts 10, 11 (cf. FIGS. 12C and 12E).

FIG. 12C shows the third step of inlaying the tabletop element 3 with pivoting into the horizontal while simultaneously applying it to the rear detent rail 7 and the rear stop. It may be seen well that the bolt axis 26 and the recess axis 39 assume an identical position through this pivoting, as soon as the detent bolt 11 plunges completely into the recess 15. In addition, the recess 15, into which the detent bolt 11 is about to plunge, is marked here. This recess 15 has a cross section which is larger than the largest cross section 16 of this detent bolt 11.

FIG. 12D shows the fourth step of inlaying the tabletop element 3 with horizontal displacement and fixing of the tabletop element 3. This horizontal displacement is performed by the locking of the fixing mechanism 20, which can have many formations and can be implemented, e.g., as an eccentric, clamping lever, snap lever, slide, and the like. However, the clamping lever 20' shown in FIGS. 10 and 11 is preferred. The detent bolt 11 shown here corresponds to the first embodiment as in preceding FIGS. 12B and 12C, in which it is immovably fixed in a corresponding opening in the tabletop element 3 by means of a press fit.

FIG. 12E shows the third step of inlaying the tabletop element 3 with pivoting into the horizontal while simultaneously applying a detent bolt 11 to the rear detent rail 7 and the rear stop. The detent bolt 11 shown here corresponds to a second embodiment, in which it is fixed so it is rotatable around the bolt axis 26 in a corresponding opening in the tabletop element 3 by means of a countersunk, soldered, or spot-welded disc. In addition, the recess 15 into which the detent bolt 11 is about to plunge is marked here. This recess 15 has a cross section which is larger than the largest cross section 16 of this detent bolt 11.

FIG. 12F shows the fourth step of inlaying the tabletop element with horizontal displacement and fixing of the tabletop element using a detent bolt according to a third embodiment. The detent bolt 11 shown here corresponds to a third embodiment, in which it is fixed so it is rotatable around the bolt axis 26 in a corresponding opening in the tabletop element 3 by means of a clip ring.

The detent bolts 10,11 are particularly preferably implemented as captive and are connected fixed in place to the respective tabletop element 3. Therefore, each detent bolt 10,11 can be fixed individually on the tabletop element 3, in that it is fixed immovably, e.g., by means of a press fit and/or by means of application of adhesives, welding, and/or soldering, at a specific location of a tabletop element 3. Alternatively, the detent bolts 10,11 can also be implemented as rotatable around their bolt axis 26 and nonetheless can be connected fixed in place to the tabletop element 3, which can also be achieved by riveting the detent bolts 10,11 to the tabletop elements 3, for example.

The at least one clamping lever 20' of the tabletop elements 3 is preferably arranged on a lower side 21 of the tabletop elements 3 and arranged so it is pivotable toward a table inner side 22 or toward a table outer side 23 of the stop surface 19. Arbitrary other arrangements of the clamping lever 20' in conjunction with the practically arbitrary arrangement of the detent rails 6,6',7,7' and detent openings 8,8',9,9' will be selected by a person skilled in the art depending on the situation and the tabletop elements 3 will thus be fastened on the frame 2 by means of spreading or blocking. Depending on the type of fastening, the attachment of a spring to those detent bolts 10, 11 and/or detent rails 6,6',7,7' which are arranged on the side opposite to the fixing mechanism 20 of a tabletop element 3 (but also on the lower side 21) is recommended.

As shown, each tabletop element 3 comprises at least one fixing mechanism 20 spaced apart from the detent bolt, which fixes the tabletop element 3 in a locking position and holds the detent bolts 10,11, which are guided parallel to a tabletop axis 27 of the tabletop element 3 (cf. FIGS. 1-3 and FIG. 11), in the detent rail 6,7 in a fixing position. The detent bolt 10,11 is preferably guided in a sliding manner in the detent rail 6,7 if the detent bolt 10,11 is fixed immovably in the tabletop element 3. If the detent bolt 10,11 is fixed so it is rotatable in the tabletop element 3, it is preferably guided in a sliding and/or rolling manner. At least a part of the detent openings 8,8',9,9' is preferably implemented to fix a detent bolt 10,11 of a tabletop element 3 in a vertical direction, the detent bolts 10,11 being guided in a horizontal direction and being fixed in the vertical direction in the locking position of the tabletop element 3 in the detent openings 8,8',9,9' of the detent rails 6,6',7,7'.

A method for installing a tabletop element 3 preferably comprises the following steps:
a) applying an edge of the tabletop element 3 to a detent rail 6',7 or a frame part 5;
b) applying an edge of the tabletop element 3 to a stop, the stop being provided by frame part 4 or by a rear wall 38;
c) pivoting the tabletop element 3 in the horizontal while simultaneously applying it to the stop and the detent rail 6',7 or the frame part 5; and
d) horizontally displacing and fixing the tabletop element 3 using the fixing mechanism 20.

In the above-described method, a clamping lever 20' is preferably used as the fixing mechanism 20, the clamping lever 20' preferably being arranged on a lower side of the tabletop elements 3 and being pivoted toward a stop surface 19 or toward one of the lower detent rails 6',7' around an axis 37 during the installation of the tabletop elements 3. A clamping bow 34 is applied in a springy manner to the stop surface 19 or the detent rail 6',7' and exerts a spring force on the stop surface 19 or the detent rail 6', 7' in a closure location defined by a fixing block 35 of the clamping lever 20'.

A method for replacing a tabletop element 3 preferably comprises the following steps, which are executed before installing another tabletop element 3:
a) disengaging the fixing mechanism 20 and horizontally displacing the tabletop element 3 until it is applied to the stop and the detent rail 6',7 or the frame part 5;
b) pivoting the tabletop element 3 out of the horizontal while simultaneously applying it to the stop and the detent rail 6',7 or the frame part 5; and
c) lifting up the tabletop element 3.

Identical reference signs relate to corresponding features, even if they are not described in detail in each case. Arbitrary combinations of the embodiments and variants which are described and/or shown are within the scope of the present invention Without deviating from the gist of the present invention and therefore in accordance with the embodiments described so far, and also within a broader view of the previously described invention, a preferred laboratory table 1 comprises:
(a) at least one frame 2 having a front frame part 4 and a rear frame part 5 opposite thereto;
(b) at least one detent element 6,6',7,7' having at least one detent opening 8,8',9,9' that is implemented and arranged for insertion of a detent extension 10,11;
(c) at least one detent extension 10,11 that is implemented and arranged for insertion into one of the detent openings 8,8', 9,9' of the detent elements 6,6',7,7'; and
(d) at least one replaceable tabletop element 3 that is positionable on the at least one frame 2.

The preferred laboratory table 1 is characterized in that each one of the replaceable tabletop elements 3 comprises:
(i) at least one fixing mechanism 20 that is configured to be moved into a locking position, in which it fixes a corresponding tabletop element 3 by interacting with the front frame part 4 or with the rear frame part 5 and thereby holding at least one corresponding detent element 6,7 and detent extension 10,11 in a mutual fixing position; and
(ii) at least one detent element 6,6',7,7' or at least one detent extension 10,11, which in each case are spaced apart from the at least one fixing mechanism 20.

The preferred laboratory table 1 is further characterized in that the frame part 5,4, which is located opposite to the frame part 4,5 the fixing mechanism 20 is interacting with, comprises at least one detent element 6,7 or at least one detent extension 10,11 that in each case is configured to be brought into a mutual fixing position with a corresponding detent extension 10,11 or detent element 6,6',7,7' of the corresponding tabletop element 3, said corresponding detent extension 10,11 being guided in a said detent element 6,6',7,7' parallel to a tabletop axis 27 of the corresponding tabletop element 3.

As apparent from the above description of a preferred laboratory table 1, the expression "detent element" is a synonym to the previously utilized expression "detent rail". Both, "detent elements" and "detent rails", preferably are linearly arranged on one or both frame parts 4,5 of the frame 2 of a preferred laboratory table 1. However, a "detent element" can be very compact and only comprising a single "detent opening". More extended "detent elements" may comprise two or more "detent openings" that still are linearly arranged on one or both frame parts 4,5. Extended "detent elements" that contain more than two "detent openings" preferably are called "detent rails".

As further apparent from the above description of a preferred laboratory table 1, the expression "detent extension" is a synonym to the previously utilized expression "detent bolt". Both, "detent extensions" and "detent bolts", preferably are linearly arranged on one or both frame parts 4,5 of the frame 2 of a preferred laboratory table 1.

With respect to the replaceable tabletop elements 3 of the preferred laboratory table 1, it is preferred that the fixing mechanism 20 is configured for interaction with said front frame part 4 or rear frame part 5, the interaction being selected from the group comprising clamping (see FIGS. 10 and 11), bracing, snapping, friction fit, friction turning, and combinations of at least two of these interactions.

With respect to the preferred laboratory table 1, it is preferred that the at least one corresponding detent element 6,6',7,7' or detent extension 10,11 are configured in each case for guided moving into said mutual fixing position by drawing or pushing in a direction parallel to the tabletop axis 27 of the corresponding tabletop element 3. "Mutual moving" means that only one partner, either a detent element 6,7 or a corresponding detent extension 10,11, can be moved. "Mutual moving" also means that both partners, a detent element 6,7 and a corresponding detent extension 10,11, of a corresponding pair of partners can be moved. At the end of any such movement, a mutual fixing position of both partners of a corresponding pair of partners is reached (see FIG. 12F).

With respect to the preferred laboratory table 1, it is further preferred that after guided moving at least one of a corresponding detent element 6,6',7,7' or detent extension 10,11 into the mutual fixing position, the corresponding detent elements 6,6',7,7' and detent extensions 10,11 are holding said tabletop element 3 to the frame part 5,4, the fixing mechanism 20 is not interacting with (see e.g. FIG. 4).

With respect to the preferred laboratory table 1, it is preferred that each of the replaceable tabletop elements 3 comprises at least one detent extension 10,11 that is configured as a bolt, hook, pin, or blade and that the front frame part 4 or the rear frame part 5 comprises at least one detent element 6,6', 7,7' with at least one detent opening 8,8',9,9' that is configured to receive one detent extension 10,11 in the form of a bolt (see FIG. 12), hook, pin, or blade.

It is preferred in alternative embodiments of the present invention that the detent extensions 10,11 are implemented as captive and are connected fixed in place to a corresponding tabletop element 3 or to a front frame part 4 or rear frame part 5, preferably in a linear arrangement (not shown).

For providing the preferred laboratory table 1 with the combinatorial capacity of a modular set of tabletop elements 3, the detent openings 8,9 of the detent elements 6,7 preferably are arranged at a regular distance 12. In accordance and at the one hand, it is preferred that the replaceable tabletop elements 3 have a width 43, which at least approximately corresponds to the regular distance 12 or at least approximately corresponds to a multiple of this regular distance 12. In accordance and at the other hand, it is preferred that the replaceable tabletop elements 3 have detent extensions 10,11 that are configured as at least two front detent extensions 10 or as at least two rear detent extensions 11, the front detent extensions 10 or rear detent extensions 11 being arranged at the same regular distance 12 or in a multiple of this regular distance 12.

For safely supporting the replaceable tabletop elements 3 of such a modular set of tabletop elements 3, it is particularly preferred that the detent elements 6,6',7,7' are configured as compact elements comprising one or two detent openings 8,8',9,9'; or as elongated rails comprising more than two detent openings 8,8',9,9'.

In one particular embodiment is preferred that a first holding web 13 is arranged in the detent openings 8,8',9,9' of the detent elements 6,6',7,7' for holding a corresponding detent extension 10,11 in a vertical direction, and for guiding the corresponding detent extension 10,11 in a horizontal direction, the holding web 13 extending in the horizontal direction and being adapted to engage a groove 14 of the corresponding detent extension 10,11. Accordingly, it is preferred that the detent extensions 10,11 are configured as a bolt with a circular cross section and comprise a groove 14, whose width is adapted to a height of the first holding web 13.

In alternative embodiments of the preferred laboratory table 1, it is preferred on the one hand that the front frame part 4 and rear frame part 5 comprise detent elements 6,6',7,7' that are fastened on the opposing frame parts 4,5 so that the detent openings 8,8',9,9' of the detent elements 6,6',7,7' are oriented toward one another or away from one another. On the other hand it may be preferred that the front frame part 4 and rear frame part 5 comprise detent elements 6,6',7,7' that are fastened on the opposing frame parts 4,5 so that the detent openings 8,8',9,9' of the detent elements 6,6',7,7' are oriented in a same direction.

In a special embodiment, the preferred laboratory table 1 comprises replaceable tabletop elements 3 in an upper tabletop level 29 and/or in a lower tabletop level 30, all replaceable tabletop elements 3 being aligned essentially horizontally in an installed state.

For correct and precise interaction of the fixing mechanism 20 with one of the frame parts 4,5 of the preferred laboratory table 1, the frame 2 comprises at last one stop surface 19, which is arranged at the front or rear frame parts 4,5 and which is selected from the group of stop surfaces 19 that comprises an outer surface of a frame part 4,5, an upright web on a frame part 4,5, a web protruding beyond a frame part 4,5, a surface inside a frame part 4,5, and arbitrary combinations of these stop surfaces 19. It is however especially preferred that the at least one fixing mechanism 20 is arranged on a lower side 21 of the tabletop elements 3 and is implemented as pivotable around an axis 37 toward the stop surface 19 or toward one of the detent elements 6',7' during the installation of the tabletop elements 3.

The at least one fixing mechanism 20 of the tabletop elements 3 may be implemented according to a great variety of fixing principles that in each case are well known to the skilled person. Preferred are fixing principles that allow bringing the fixing elements into a locked arrangement without the use of a tool. Especially preferred are fixing principles that allow bringing the fixing elements into a locked arrangement and also release these fixing elements from the locked arrangement without the use of a tool. Because of the large number of appropriate fixing principles that can be selected by a person of average skill, only one preferred fixing principle is depicted in the attached drawings. Accordingly and without being exhaustive in pointing to possible embodiments, the at least one fixing mechanism 20 of the tabletop elements 3 may be implemented as:

- a clamping lever 20' with a clamping bow 34, the clamping bow 34 being configured to apply in a springy manner to the stop surface 19 or the detent element 6',7' and exerting a spring force on the stop surface 19 or the detent element 6',7' (see FIGS. 10 and 11); or
- a bracing claw with two claw members, the claw members being configured to apply in a springy manner to two surfaces, selected from stop surfaces and surfaces of detent elements and exerting a spring force on two of said surfaces (not shown); or
- a snap-fit with a snap portion, the snap portion being configured to apply in a springy manner to a stop surface or a detent element and exerting a spring force on said surface (not shown); or
- a friction member with at least one friction surface, the friction surfaces being configured to apply a friction fit to at least one stop surface or detent element and exerting a spring force on said surfaces (not shown); or
- a turning key with at least on key bit, the key bits being configured to be moved into locking position on at least one stop surface or detent element (not shown).

The preferred laboratory table 1 enables for carrying out a method for providing or assembling a laboratory table 1. As described before, such a laboratory table 1 comprises:

(a) at least one frame 2 having a front frame part 4 and a rear frame part 5 opposite thereto;

(b) at least one detent element 6,6',7,7' having at least one detent opening 8,8',9,9' that is implemented and arranged for insertion of a detent extension 10,11;

(c) at least one detent extension 10,11 that is implemented and arranged for insertion into one of the detent openings 8,8', 9,9' of the detent elements 6,6',7,7'; and (d) at least one replaceable tabletop element 3 that is positionable on the at least one frame 2, that comprises at least one fixing mechanism 20 for holding at least one corresponding detent element 6,7 and detent extension 10,11 in a mutual fixing position.

This method is characterized in that a replaceable tabletop element 3 is positioned on the frame 2 and at least one detent element 6,6',7,7' or at least one detent extension 10,11 of the tabletop element 3 is brought into a mutual fixing position with a corresponding detent extension 10,11 or a corresponding detent element 6,6',7,7' of the front frame part 4 or the rear frame part 5, whereby the detent extension 10,11 is guided in the corresponding detent element 6,6',7,7' parallel to a tabletop axis 27 of the tabletop element 3.

This method is further characterized in that the fixing mechanism 20 is moved into a locking position, in which the fixing mechanism 20 interacts with the front frame part 4 or the rear frame part 5 and fixes a corresponding tabletop element 3 on the frame part 4,5 the fixing mechanism 20 is interacting with; the detent extension 10,11 sliding in the corresponding detent element 6,7 in a direction parallel to a tabletop axis 27 of the corresponding tabletop element 3 into a fixing position and being fixed there.

For providing or assembling a special embodiment of the preferred laboratory table 1, a number of tabletop elements 3 are aligned essentially horizontally and are installed in this frame 2 in an upper tabletop level 29 and/or in a lower tabletop level 30.

Deviating from the embodiments as shown in the Figures, a frame part for supporting detent elements 6,7 or detent extensions 10,11 can be configured as an intermediate frame part that is located between the front and rear frame parts 4,5. It is however still preferred that the detent elements 6,7 or detent extensions 10,11 of the intermediate frame part can be brought into a mutual fixing position with the corresponding detent elements 6,7 or detent extensions 10,11 of a replaceable tabletop element 3, and that the corresponding detent elements 6,7 or detent extensions 10,11 of a replaceable tabletop element 3 still are spaced apart from the at least one fixing mechanism 20.

List of reference numerals

| | |
|---|---|
| 1 | laboratory table |
| 2 | frame |
| 3 | replaceable tabletop element |
| 4 | front frame part |
| 5 | rear frame part |
| 6 | upper front detent rail, upper front detent element |
| 6' | lower front detent rail, lower front detent element |
| 7 | upper rear detent rail, upper rear detent element |
| 7' | lower rear detent rail, lower rear detent element |
| 8 | upper front detent opening |
| 8' | lower front detent opening |
| 9 | upper rear detent opening |
| 9' | lower rear detent opening |
| 10 | front detent bolt, detent extension |
| 11 | rear detent bolt, detent extension |
| 12 | distance |
| 13 | first holding web |
| 13' | second holding web |
| 14 | groove |
| 15 | recess |
| 15' | oblong hole |
| 16 | largest cross section of 10, 11 |
| 17 | reduced cross section of 10, 11 |
| 18 | constriction |
| 19 | stop surface |
| 20 | fixing mechanism |
| 20' | clamping lever |
| 21 | lower side of 3 |
| 22 | table inner side |
| 23 | table outer side |
| 24 | further frame part |
| 25 | further frame part |
| 26 | bolt axis |
| 27 | tabletop axis |
| 28 | infeed chamfer |
| 29 | upper tabletop level |
| 30 | lower tabletop level |
| 31 | holding rail |
| 32 | detent cam |
| 33 | reinforcement bracket |
| 34 | clamping bow |
| 35 | fixing block |
| 36 | handle |
| 37 | axis |
| 38 | rear wall |
| 39 | recess axis |
| 40 | cutout |
| 41 | over-twisting guard |
| 42 | holding portion |
| 43 | width of 3 |
| 44 | joint |

The invention claimed is:

1. A laboratory table (1), comprising:
   (a) one frame (2) having a front frame part (4) and a rear frame part (5) located opposite thereto;
   (b) one replaceable tabletop element (3) that is positionable on the at least one frame (2);
   (c) one detent element (6,6',7,7') having at least one detent opening (8,8',9,9') that is implemented and arranged for insertion of a detent extension (10,11) and that is located at one or both of the front or rear frame parts (4,5) or at a replaceable tabletop element (3);
   (d) one detent extension (10,11) that is implemented and arranged for insertion into one of the detent openings (8,8',9,9') of the detent elements (6,6',7,7') and that is located at a replaceable tabletop element (3) or at one or both of the front or rear frame parts (4,5);
   wherein each one of the replaceable tabletop elements (3) comprises
   at least one fixing mechanism (20) that is configured to be moved into a locking position, in which it fixes the replaceable tabletop element (3) to the frame (2) by interacting with the front frame part (4) or with the rear frame part (5) and thereby holding at least one corresponding detent element (6,7) and detent extension (10, 11) of the front or rear frame part (4,5) and the replaceable tabletop element (3) in a mutual fixing position, the at least one detent element (6,6',7,7') or at least one detent extension (10,11) in each case being spaced apart from the at least one fixing mechanism (20); and
   wherein at least one detent extension (10,11) of the rear or front frame part (5,4), which is located opposite to the front or rear frame part (4,5) the fixing mechanism (20) is interacting with, or at least one detent extension (10,11) of said tabletop elements (3) is in mutual fixing position with the corresponding detent element (6,6',7,7') of said tabletop elements (3) or of the rear or front frame part (5,4), said at least one detent extension (10,11) being guided in said detent element (6,6', 7,7') parallel to a tabletop axis (27) of the corresponding tabletop element (3).

2. The laboratory table (1) according to claim 1, wherein the fixing mechanism (20) is configured for interaction with said front frame part (4) or rear frame part (5), the interaction being selected from the group comprising clamping, bracing, snapping, friction fit, friction turning, and combinations of at least two of these interactions.

3. The laboratory table (1) according to claim 1, wherein the at least one corresponding detent element (6,6', 7,7') or detent extension (10,11) are configured in each case for guided moving into said mutual fixing position by drawing or pushing in a direction parallel to the tabletop axis (27) of the corresponding tabletop element (3).

4. The laboratory table (1) according to claim 3, wherein after guided moving at least one of a corresponding detent element (6,6',7,7') or detent extension (10,11) into the mutual fixing position, the corresponding detent elements (6,6',7,7') and detent extensions (10,11) are holding said tabletop element (3) to the frame part (5,4), the fixing mechanism (20) is not interacting with.

5. The laboratory table (1) according to claim 1, wherein each of the replaceable tabletop elements (3) comprises at least one detent extension (10,11);
   and wherein the front frame part (4) or the rear frame part (5) comprises at least one detent element (6,6',7,7') with at least one detent opening (8,8',9,9') that is configured to receive one detent extension (10,11).

6. The laboratory table (1) according to claim 1, wherein the detent extensions (10,11) are implemented as captive and are connected fixed in place to a corresponding tabletop element (3) or to a front frame part (4) or rear frame part (5).

7. The laboratory table (1) according to claim 1, wherein the detent openings (8,9) of the detent elements (6,7) are arranged at a regular distance (12).

8. The laboratory table (1) according to claim 7, wherein the replaceable tabletop elements (3) have a width (43), which at least approximately corresponds to the regular distance (12) or at least approximately corresponds to a multiple of this regular distance (12).

9. The laboratory table (1) according to claim 7, wherein the replaceable tabletop elements (3) have detent extensions (10,11) that are configured as at least two front detent extensions (10) or as at least two rear detent extensions (11), the front detent extensions (10) or rear detent extensions (11) being arranged at the same regular distance (12) or in a multiple of this regular distance (12).

10. The laboratory table (1) according to claim 1,
wherein the detent elements (6,6',7,7') are configured as:
compact elements comprising one or two detent openings (8,8',9,9'); or
elongated rails comprising more than two detent openings (8,8',9,9').

11. The laboratory table (1) according to claim 1,
wherein a first holding web (13) is arranged in the detent openings (8,8',9,9') of the detent elements (6,6',7,7') for holding a corresponding detent extension (10,11) in a vertical direction, and for guiding the corresponding detent extension (10,11) in a horizontal direction, the holding web (13) extending in the horizontal direction and being adapted to engage a groove (14) of the corresponding detent extension (10,11).

12. The laboratory table (1) according to claim 11,
wherein the detent extensions (10,11) are configured as a bolt with a circular cross section and comprise a groove (14), whose width is adapted to a height of the first holding web (13).

13. The laboratory table (1) according to claim 1,
wherein the front frame part (4) and rear frame part (5) comprise detent elements (6,6',7,7') that are fastened on the opposing frame parts (4,5) so that the detent openings (8,8',9,9') of the detent elements (6,6',7,7') are oriented toward one another or away from one another.

14. The laboratory table (1) according to claim 1,
wherein the front frame part (4) and rear frame part (5) comprise detent elements (6,6',7,7') that are fastened on the opposing frame parts (4,5) so that the detent openings (8,8',9,9') of the detent elements (6,6',7,7') are oriented in a same direction.

15. The laboratory table (1) according to claim 1,
wherein the laboratory table (1) comprises replaceable tabletop elements (3) in an upper tabletop level (29) and/or in a lower tabletop level (30), all replaceable tabletop elements (3) being aligned essentially horizontally in an installed state.

16. The laboratory table (1) according to claim 1,
wherein the frame (2) comprises at last one stop surface (19), which is arranged at the front or rear frame parts (4,5) and which is selected from the group of stop surfaces (19) that comprises an outer surface of a frame part (4,5), an upright web on a frame part (4,5), a web protruding beyond a frame part (4,5), a surface inside a frame part (4,5), and combinations of these stop surfaces (19).

17. The laboratory table (1) according to claim 16,
wherein the at least one fixing mechanism (20) is arranged on a lower side (21) of the tabletop elements (3) and is implemented as pivotable around an axis (37) toward the stop surface (19) or toward one of the detent elements (6',7') during the installation of the tabletop elements (3).

18. The laboratory table (1) according to claim 17,
wherein the at least one fixing mechanism (20) of the tabletop elements (3) is implemented as a clamping lever (20') with a clamping bow (34), the clamping bow (34) being configured to apply in a springy manner to the stop surface (19) or the detent element (6',7') and exerting a spring force on the stop surface (19) or the detent element (6',7').

19. A method for providing a laboratory table (1),
wherein the laboratory table (1) comprises:
(a) one frame (2) having a front frame part (4) and a rear frame part (5) located opposite thereto;
(b) one replaceable tabletop element (3) that is positionable on the at least one frame (2) and that comprises at least one fixing mechanism (20) for holding at least one corresponding detent element (6,7) and detent extension (10,11) in a mutual fixing position;
(c) at least one detent element (6,6',7,7') having at least one detent opening (8,8',9,9') that is implemented and arranged for insertion of a detent extension (10,11) and that is located at one or both of the front or rear frame parts (4,5) or at a replaceable tabletop element (3);
(d) at least one detent extension (10,11) that is implemented and arranged for insertion into one of the detent openings (8,8',9,9') of the detent elements (6,6',7,7') and that is located at a replaceable tabletop element (3) or at one or both of the front or rear frame parts (4,5);
wherein a replaceable tabletop element (3) is positioned on the frame (2) and at least one detent element (6,6',7,7') or at least one detent extension (10,11) of the tabletop element (3) is brought into a mutual fixing position with a corresponding detent extension (10,11) or a corresponding detent element (6,6',7,7') of the front frame part (4) or the rear frame part (5), whereby the detent extension (10,11) is guided in the corresponding detent element (6,6',7,7') parallel to a tabletop axis (27) of the tabletop element (3);
and wherein the fixing mechanism (20) is moved into a locking position, in which the fixing mechanism (20) interacts with the front frame part (4) or the rear frame part (5) of the fame (2) and fixes a corresponding tabletop element (3) on said front or rear frame part (4,5) the fixing mechanism (20) is interacting with; the detent extension (10,11) sliding in the corresponding detent element (6,7) in a direction parallel to a tabletop axis (27) of the corresponding tabletop element (3) into a fixing position and being fixed there.

20. The method according to claim 19,
wherein a number of tabletop elements (3) are aligned essentially horizontally and are installed in this frame (2) in an upper tabletop level (29) and/or in a lower tabletop level (30).

* * * * *